(12) United States Patent
Stefan et al.

(10) Patent No.: US 8,511,625 B2
(45) Date of Patent: Aug. 20, 2013

(54) HOLDING DEVICE FOR MEDICAL INSTRUMENTS

(75) Inventors: Jochen Stefan, Wald (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 12/961,201

(22) Filed: Dec. 6, 2010

(65) Prior Publication Data

US 2011/0150564 A1   Jun. 23, 2011

(30) Foreign Application Priority Data

Dec. 23, 2009  (DE) .......................... 10 2009 060 494

(51) Int. Cl.
*F16M 11/14* (2006.01)

(52) U.S. Cl.
USPC .................................. 248/181.1; 248/288.51

(58) Field of Classification Search
USPC .................. 248/181.1, 181.2, 288.31, 288.51
See application file for complete search history.

(56) References Cited

U.S. PATENT DOCUMENTS

| | | | |
|---|---|---|---|
| 2,533,494 A | 12/1950 | Mitchell, Jr. | |
| 2,859,983 A * | 11/1958 | May .................. | 285/90 |
| 2,861,501 A * | 11/1958 | Strelakos ..................... | 359/802 |
| 4,974,802 A * | 12/1990 | Hendren ..................... | 248/181.1 |
| 6,352,228 B1 * | 3/2002 | Buerklin ..................... | 248/181.1 |
| 6,767,153 B1 | 7/2004 | Holbrook | |
| 7,007,901 B2 * | 3/2006 | Kondo ............................. | 248/75 |
| 2009/0232590 A1 * | 9/2009 | Ersoy et al. .................... | 403/135 |
| 2009/0308993 A1 * | 12/2009 | Chang ........................ | 248/176.3 |

FOREIGN PATENT DOCUMENTS

| | | |
|---|---|---|
| DE | 1289684 B | 2/1969 |
| DE | 1292952 B | 4/1975 |
| DE | 29511900 U1 | 9/1995 |
| DE | 19521060 A1 | 12/1996 |
| DE | 29521305 U1 | 12/1996 |
| EP | 1098933 A2 | 12/1986 |
| EP | 0868885 A1 | 10/1998 |
| WO | 9105960 A1 | 5/1991 |

OTHER PUBLICATIONS

European Search Report; Application No. EP 10 01 5163; Apr. 14, 2011; 6 pages.

* cited by examiner

*Primary Examiner* — Gwendolyn Baxter
(74) *Attorney, Agent, or Firm* — St. Onge Steward Johnston & Reens LLC

(57) ABSTRACT

A holding device for medical instruments, with a bracket on which at least one medical instrument can be affixed and with at least one joint to position the bracket and/or the medical instrument, so that the at least one joint is configured as a ball and socket joint that is provided with at least one bearing shell and a pivot ball and that can be converted between a position that releases the joint and one that blocks the joint. To provide a holding device for medical instruments that is simple to operate, makes possible a rapid blocking and releasing of the at least one joint, and in addition ensures that unintentional release of the blocking is excluded to the greatest extent possible, it is proposed with the invention that the bearing shell should be of rigid configuration and the pivot ball should be capable of being affixed in the bearing shell by clamping by at least one blocking element.

14 Claims, 3 Drawing Sheets

HOLDING DEVICE FOR MEDICAL INSTRUMENTS

CROSS-REFERENCE TO RELATED APPLICATIONS

The present application claims priority of German patent application No. 10 2009 060 494.4 filed on Dec. 23, 2009, the content of which is incorporated herein by reference.

FIELD OF THE INVENTION

The invention relates to a holding device for medical instruments, with a bracket on which at least one medical instrument can be affixed and with at least one joint to position the bracket and/or the medical instrument, such that the at least one joint is configured as a ball joint equipped with at least one bearing shell and a pivot ball that can be converted between a position that releases the joint and one that blocks the joint.

BACKGROUND OF THE INVENTION

Holding devices of this type are often required in performing surgical procedures in order to hold medical instruments of various types, such as retractors, video cameras or endoscopes, in a particular position for extended periods. Thanks to the jointed configuration of the holding devices it is possible for the surgeon to precisely position the medical instrument held by the bracket and to fix the selected position of the holding device by blocking the joint or joints of the bracket.

A generic holding device is known for example from DE 295 21 305 U1. In this known holding device, the pivot ball is pressed against the bearing shell by a spring-loaded pressure plate, which in turn constitutes a part of the bearing shell. To block the joint, the pressure plate is coupled with a piezoelectric actuator that expands on the application of electric current and thus increases the pressure of the pressure plate on the pivot ball until the pivot ball is affixed by clamping.

With this known structure it is possible to affix the ball and socket joint securely, but the structure has the disadvantage that it is no longer possible to block the joint in the event of a power failure. In addition, structures with a partial spring-loaded bearing shell have the disadvantage that with an axial force on the pivot ball that is directed against the force direction of the spring-loaded bearing shell, the joint can unintentionally be released.

SUMMARY OF THE INVENTION

On this basis it is the object of the invention to provide a holding device for medical instruments of the aforementioned type, which is simple to operate, makes possible rapid blocking and release of the at least one joint, and in addition ensures that unintentional release of the blocking is largely excluded.

This object is fulfilled according to the invention in such a way that the bearing shell is of rigid configuration and the pivot ball can be affixed in the bearing shell by clamping with at least one blocking element.

As a result of the inventive configuration of a blocking element by which the pivot ball is held by clamping in the bearing shell that is rigid, that is, largely unchangeable in its configuration, it is guaranteed that, even with an axial force exerted on the pivot ball, the bearing shell enclosing the pivot ball remains unchanged and that the at least one blocking element can block the pivot ball by clamping.

According to a practical embodiment of the invention, it is proposed that in the bearing shell at least one recess should be configured by which at least one blocking element can be inserted in each case in the joint in such a way that the blocking element presses the pivot ball by clamping against the bearing shell to block the joint. The at least one blocking element, which can be inserted via a recess in the bearing shell, makes possible the inventive blocking of the pivot ball without the necessity of modifying the bearing shell in its position or dimensions for clamping purposes.

With a preferred embodiment of the invention, it is further proposed that the bearing shell should be configured of two parts consisting of an upper bearing shell and a lower bearing shell and that the at least one recess for at least one blocking element in each case should be configured in the lower bearing shell. This embodiment constitutes a structure for configuring the bearing shell that is especially easy to handle in production and assembly.

To achieve a uniform siting of the blocking elements on the pivot ball and thus a uniform clamping and affixing of the pivot ball, it is proposed with the invention that four recesses should be configured, distributed around the periphery of the bearing shell, each for at least one blocking element in the bearing shell.

Every blocking element is advantageously pre-tensioned by a spring element in the direction toward the site on the pivot ball in order to ensure a durable siting of the blocking elements on the pivot ball.

To facilitate the clamping by pressing the pivot ball into the bearing shell by means of the blocking elements, it is further proposed with the invention that each blocking element should be of conical configuration, at least in the area of the site on the pivot ball, while a clamping coating can be applied advantageously on each blocking element in the area of the site of the blocking element on the pivot ball. A material with a high friction resistance can be used, for example, as the clamping coating to prevent relative movement between the blocking element and the pivot ball.

To release the blocking clamping of the pivot ball, it is proposed with the invention that each blocking element should be capable of shifting by means of at least one actuating element into a position that releases the joint. According to experience, the at least one actuating element should be configured so that it withdraws every blocking element from the site on the pivot ball.

According to a practical embodiment of the invention it is proposed that all blocking elements should be capable of shifting by means of a common actuating element into a position that releases the joint to ensure a rapid, uniform release of the blocking.

It is further proposed with the invention that the at least one actuating element should be capable of actuation by applying an electric current, while the at least one actuating element advantageously should be capable of actuation by at least one piezoelectric actuator. Piezoelectric actuators are distinguished in that, when an electric current is applied, they react with a change in length, for example an expansion. By extending the piezoelectric actuator that has been charged with electric current, the blocking elements are drawn away from the pivot ball by the at least one actuating element and thus the joint is released again.

It is finally proposed with the invention that the ball and socket joint should be insulated from the environment by at least one insulating element that is contiguous with the pivot ball to obtain a joint that is protected from external influences such as moisture and dirt in particular.

Further properties and advantages of the invention can be seen from the appended drawings, in which one embodiment of an inventive holding device for medical instruments is presented only by way of example, with restricting the invention to this embodiment.

DETAILED DESCRIPTION OF THE INVENTION

Figure 1:
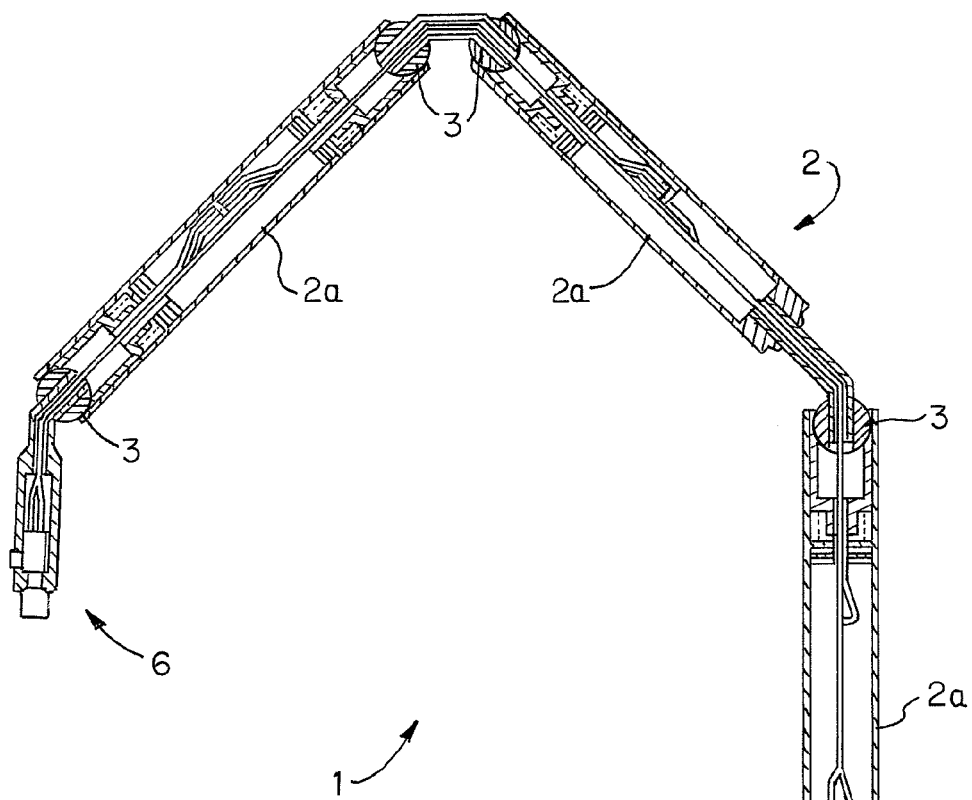
FIG. 1 shows a holding device for medical instruments according to the state of the art.

FIG. 1 shows a holding device 1 for medical instruments according to the state of the art.

This holding device 1 consists essentially of a bracket 2 consisting of several bracket parts 2a, where the individual bracket parts 2a of the bracket are connected with one another so that they can pivot with respect to one another by means of joints configured as ball joints 3.

Holding devices 1 of this type are frequently required in executing surgical procedures in order to hold medical instruments of various types, such as retractors, video cameras or endoscopes, in a certain position for an extended period. As a result of the jointed configuration of the holding device 1, it is possible for the surgeon to precisely position the medical instrument and to affix the selected position of the holding device 1 by blocking the joint 3 or joints 3. In addition to endoscopic surgery, such holding devices 1 also find application in open surgery or invasive procedures.

In the area of its proximal end, the bracket 2 can be secured, for example on an operating table, by means of a jig 4. On the distal end the bracket 2 comprises an instrument insertion 6 for inserting the medical instrument that is to be positioned by means of the holding device 1.

Alternatively to the structure of the bracket 2 illustrated in FIG. 1 consisting of several bracket parts 2a that are coupled one behind the other and are connected with one another by joints 3, it is also possible of course to configure the bracket 2 with several arms in such a manner that several bracket arms extend from one joint 3 in various directions. These bracket parts 2a in turn can be coupled again by joints 3 with additional bracket parts 2a and can each be equipped on their distal ends with instrument insertions 6 for inserting the medical instruments that are to be positioned by the holding device 1.

Figure 2:
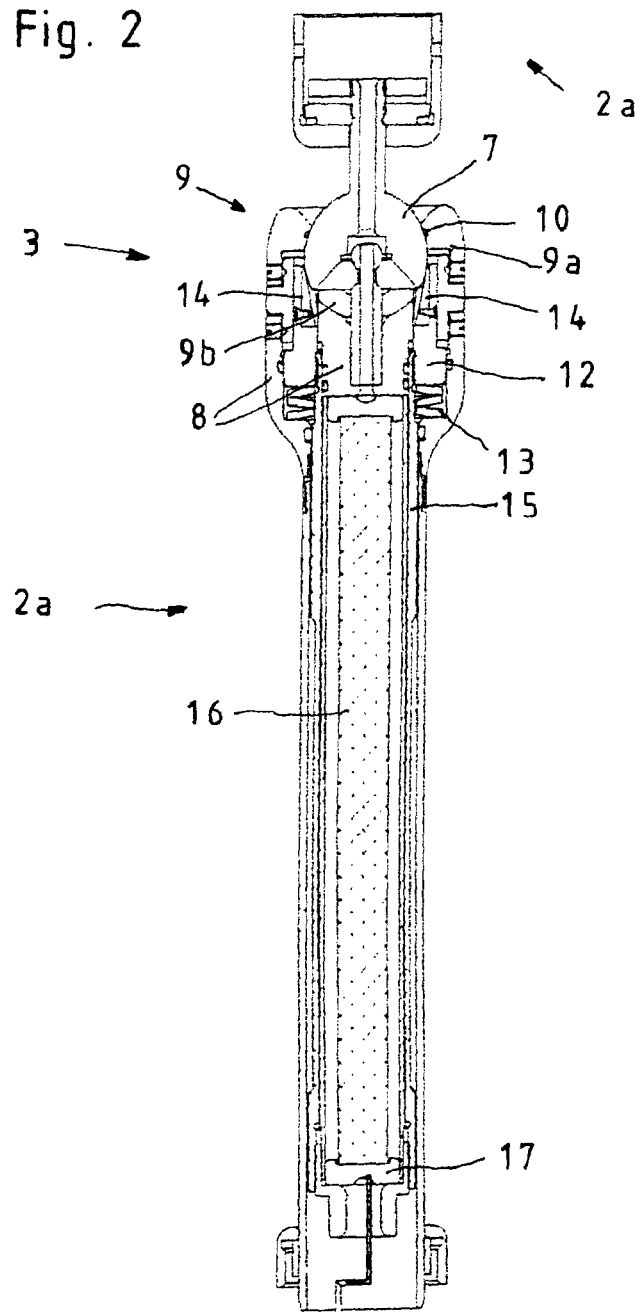
FIG. 2 shows a sectioned view of a ball joint for an inventive holding device for medical instruments.
Figure 3:
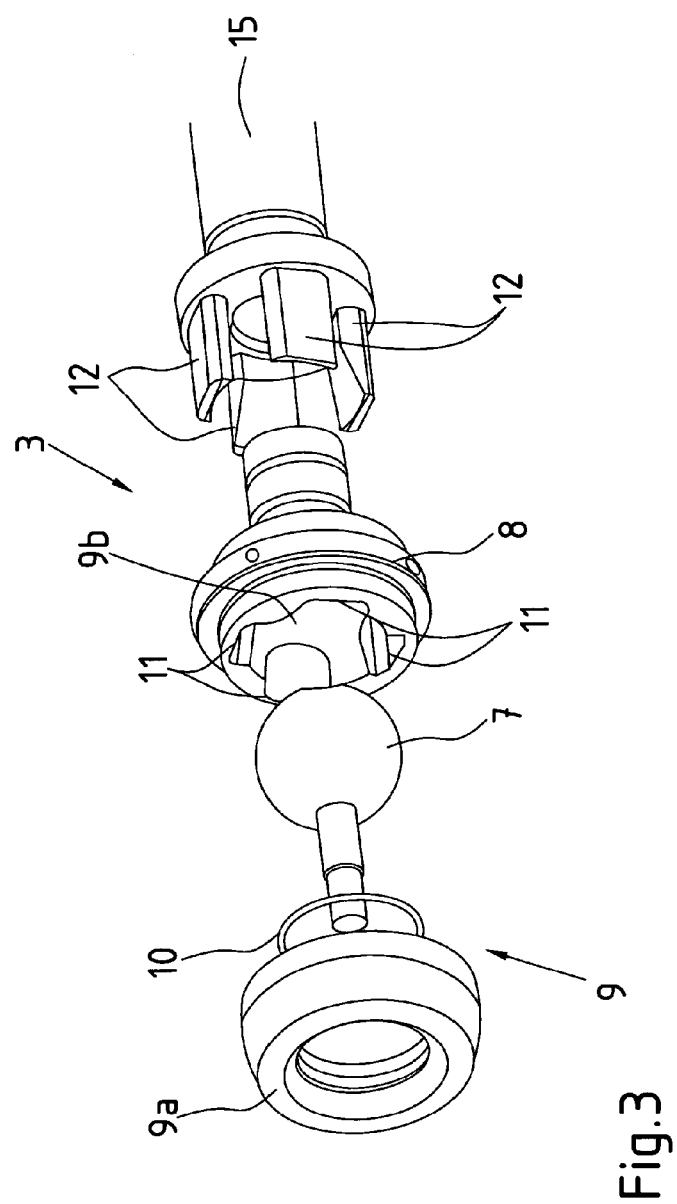
FIG. 3 shows a perspective view of the ball joint according to FIG. 2.

The structure of the ball and socket joints 3 can be seen in FIGS. 2 and 3.

As shown in FIGS. 2 and 3, the ball and socket joints 3 consist of a pivot ball 7, which is mounted to pivot in a bearing shell 9 configured in a joint housing 8. In the illustrated embodiment the bearing shell 9 is of two-part configuration consisting of an upper bearing shell 9a and a lower bearing shell 9b. The bearing shell 9 is rigidly positioned in the joint housing 8; that is, the upper bearing shell 9a and the lower bearing shell 9b, when the ball and socket joint 3 is in assembled state, are not movable with respect to one another in the axial direction of the joint 3; therefore no enlargement or reduction of the movement play of the pivot ball 7 is possible in the bearing shell 9 because of a movement of the bearing shell 9.

As can also be seen from FIGS. 2 and 3, the ball and socket joint 3 in the upper bearing shell 9a comprises an insulating element 10 that is contiguous with the pivot ball 7 in order to shield the joint 3 from outside and thus from external influences such as moisture and dirt.

To be able to affix the ball and socket joint 3 in the particular required position of the bracket 2, recesses 11 are configured in the lower bearing shell 9b by which blocking elements 12 can be inserted into the ball and socket joint 3 in such a way that the blocking elements 12 are contiguous with the pivot ball 7 and press the pivot ball into the bearing shell 9 clamping it. As can be seen from comparing the images in FIGS. 2 and 3, the blocking elements 12 in the illustrated embodiment are positioned so that they attack the pivot ball 7 approximately tangentially.

Alternatively to the illustrated embodiment, it is also possible of course to arrange the blocking elements 12 in such a way that they impact the pivot ball 7 primarily radially.

The clamping force to affix the pivot ball 7 is applied by spring elements 13 by which each blocking element 12 is pre-tensed in the direction toward the site on the pivot ball 7.

To facilitate the clamping impression of the pivot ball 7 into the bearing shell 9 by means of the blocking elements 12, each blocking element 12 is configured conically at least in the area of the site on the pivot ball 7, so that with the illustrated embodiment a clamping coating 14 is applied on each blocking element 12 in the area of the siting of the blocking element 12 on the pivot ball 7. A material with a high friction resistance, for example, can be used as clamping coating 13 in order to prevent a relative movement between the blocking element 12 and the pivot ball 7.

The configuration of the ball and socket joint 3 with the spring-loaded blocking elements 12 that can be inserted in the inside of the joint 3 shows that, even in exerting external axial forces on the pivot ball 7 that act contrary to the pressure direction of the spring elements 13, the blocking elements 12 are contiguous with the pivot ball 7 with a durable clamping action, because the bearing shell 9 is positioned rigidly in the joint housing 8 and thus absorbs the exerted axial forces without its own axial displacement.

The blocking elements 12 are released, as is therefore the blocking of the joint 3 as well, by an actuation element 15 that engages with the blocking elements 12 and that is configured in the embodiment shown in FIG. 2 as a tube mounted inside the joint housing 8 and engaging with all blocking elements 12. The blocking elements 12 can be withdrawn from their site on the pivot ball 7 contrary to the spring force of the spring elements 13 by the actuation element 15, so that the pivot ball 7 is mounted in the bearing shell 9 so that it can freely pivot again.

In the illustrated embodiment, all blocking elements 12 are moved by means of a common actuation element 15 into the position that releases the joint 3. It is also possible of course to provide one actuation element 15 for each blocking element 12.

The actuating element 15 is actuated in the illustrated embodiment by applying an electric current. For this purpose the actuation element 15 is coupled with a piezoelectric actuator 16 that expands on the application of an electric current.

In the embodiment illustrated in FIG. 2, the piezoelectric actuator 16 is supported on an internal central part of the rigid joint housing 8. As soon as the operator, to displace the holding device 1, impacts the piezoelectric actuator 16 with electric current, for example by a foot switch, the actuator expands because of the piezoelectric effect, that is, in FIG. 2, downward and away from the ball and socket joint 3. Consequently the actuation element 15 is likewise pressed away from the ball and socket joint 3 by an carrier element 17, with which the piezoelectric actuator 16 is contiguous on the side away from the joint 3. This, in turn, causes the blocking elements 12 that are directly coupled with the actuation element 15 to be drawn out of their site on the pivot ball 7 contrary to the pressure force of the spring element 13 and causes the joint 3 to be released.

As soon as the actuation element 15 is no longer actuated or the piezoelectric actuator 16 is no longer impacted with electric current, the spring elements 13 press the blocking elements 12 back into the clamping site on the pivot ball 7, and thus the joint 3 is again blocked. Thus this embodiment is an authentic, effective fail-safe switch, because, for example in the event of a power failure or another failure of the actuation element 15, the blocking elements 12 always remain in their clamping site on the pivot ball 7, which also blocks the joint 3, or assume again the position that secures the joint 3.

A holding device for medical instruments as heretofore described is characterized in that in addition to simple operation, rapid blocking and release of the at least one joint 3 is possible and thus there is a guarantee that any unintentional release of the blocking of the joint 3 is excluded to the greatest extent possible.

What is claimed is:

1. A holding device for medical instruments, with a bracket on which at least one medical instrument can be affixed and with at least one joint to position the bracket and the medical instrument, wherein the at least one joint is configured as a ball and socket joint that is provided with at least one bearing shell and a pivot ball and that is adapted to be converted between a position that releases the joint for movement and one that blocks the joint against movement, the bearing shell bearing on the pivot ball, the bearing shell and the pivot ball being disposed in a housing, the bearing shell being of rigid configuration, the pivot ball being axially stationary relative to said housing, wherein the pivot ball is adapted to be releasably locked against movement by clamping in the bearing shell by at least one blocking element disposed within said housing;

wherein, in the bearing shell having a plurality of recesses about an inner periphery, at least one recess is configured by which in each case at least one blocking element is adapted to be inserted into the at least one recess in such a way that the blocking element presses the pivot ball to block the joint by clamping against the bearing shell.

2. The holding device according to claim 1, wherein the bearing shell is of two-part configuration, consisting of an upper bearing shell and a lower bearing shell and the at least one recess in each case is configured for the at least one blocking element in the lower bearing shell.

3. The holding device according to claim 2, wherein four recesses are configured over the periphery of the bearing shell, each for the at least one blocking element in the bearing shell.

4. The holding device according to claim 1, wherein four recesses are configured over the periphery of the bearing shell, each recess adapted for receiving the at least one blocking element in the bearing shell.

5. The holding device according to claim 1, wherein each blocking element is pre-tensed by a spring element toward a site on the pivot ball.

6. The holding device according to claim 1, wherein a clamping coating is applied on each blocking element in an area where the blocking element clamps on the pivot ball.

7. The holding device according to claim 1, wherein each blocking element is of conical configuration, at least in the area of the site on the pivot ball.

8. The holding device according to claim 1, wherein each blocking element can be converted by at least one actuation element into a position that releases the joint.

9. The holding device according to claim 8, wherein the at least one actuation element withdraws each said blocking element from the pivot ball.

10. The holding device according to claim 9, wherein all blocking elements can be converted by a common actuation element into a position that releases the joint.

11. The holding device according to claim 8, wherein each blocking element can be converted by a common actuation element into a position that releases the joint.

12. The holding device according to claim 8, wherein the at least one actuation element can be actuated by applying an electric current.

13. The holding device according to claim 12, wherein the at least one actuation element can be actuated by at least one piezoelectric actuator.

14. The holding device according to claim 1, wherein the ball and socket joint is insulated from an environment external to said holding device by at least one insulating element that is contiguous with the pivot ball.

* * * * *